(12) United States Patent
Krutmann et al.

(10) Patent No.: US 12,409,116 B2
(45) Date of Patent: Sep. 9, 2025

(54) LYCOPENE COMPOSITIONS AND METHODS FOR PROTECTING SKIN AGAINST ULTRAVIOLET RADIATION

(71) Applicant: LYCORED LTD., Be'er Sheva (IL)

(72) Inventors: Jean Krutmann, Düsseldorf (DE); Yoav Sharoni, Omer (IL); Joseph Levy, Omer (IL); Karin Linnewiel Hermoni, Tenafly, NJ (US)

(73) Assignee: LYCORED LTD., Be'er Sheva (IL)

( * ) Notice: Subject to any disclaimer, the term of this patent is extended or adjusted under 35 U.S.C. 154(b) by 0 days.

(21) Appl. No.: 18/674,999

(22) Filed: May 27, 2024

(65) Prior Publication Data

US 2024/0307278 A1 Sep. 19, 2024

Related U.S. Application Data

(62) Division of application No. 17/262,198, filed as application No. PCT/IL2019/050833 on Jul. 23, 2019, now abandoned.

(60) Provisional application No. 62/701,899, filed on Jul. 23, 2018.

(51) Int. Cl.
```
A61K 8/31       (2006.01)
A23L 33/15      (2016.01)
A61K 8/365      (2006.01)
A61K 9/00       (2006.01)
A61K 31/015     (2006.01)
A61K 31/191     (2006.01)
A61K 31/355     (2006.01)
A61Q 19/08      (2006.01)
```

(52) U.S. Cl.
CPC ............... *A61K 8/31* (2013.01); *A23L 33/15* (2016.08); *A61K 8/365* (2013.01); *A61K 9/0053* (2013.01); *A61K 31/015* (2013.01); *A61K 31/191* (2013.01); *A61K 31/355* (2013.01); *A61Q 19/08* (2013.01); *A61K 2800/522* (2013.01); *A61K 2800/92* (2013.01)

(58) Field of Classification Search
CPC ........ A23L 33/15; A61K 8/365; A61K 31/355
See application file for complete search history.

(56) References Cited

U.S. PATENT DOCUMENTS

| | | | |
|---|---|---|---|
| 3,920,834 A | 11/1975 | Klaui | |
| 5,290,605 A | 3/1994 | Shapira | |
| 6,110,478 A | 8/2000 | Harang | |
| 8,460,718 B2 | 6/2013 | Zelkha et al. | |
| 2003/0161791 A1* | 8/2003 | Bentley | A61K 9/0075 424/78.17 |
| 2009/0035369 A1* | 2/2009 | Sela | A61P 27/02 424/490 |
| 2009/0176872 A1 | 7/2009 | Zelkha et al. | |
| 2016/0038440 A1 | 2/2016 | Levy et al. | |
| 2017/0035713 A1 | 2/2017 | Zelkha et al. | |
| 2017/0354704 A1* | 12/2017 | Zelkha | A61P 39/06 |
| 2022/0079901 A1 | 3/2022 | Zelkha et al. | |

FOREIGN PATENT DOCUMENTS

| | | |
|---|---|---|
| CN | 1649574 A | 8/2005 |
| CN | 102355894 A | 2/2012 |
| CN | 107106625 A | 8/2017 |
| CN | 108245496 A | 7/2018 |
| EP | 2381935 B1 | 6/2016 |
| JP | 2012515198 A | 7/2012 |
| JP | 2014513075 A | 5/2014 |
| JP | 2015205882 A | 11/2015 |
| JP | 2018501305 A | 1/2018 |

OTHER PUBLICATIONS

Rosenzweig, F. (Feb. 23, 2016). One Benefit Of Eating Tomatoes You've Never Heard Of. Women's Running. https://www.womensrunning.com/health/one-benefit-of-eating-tomatoes-youve-never-heard-of/.

Lycored. (n.d.). Lycored Nutrient Complex. Retrieved Jun. 1, 2022, from https://www.lycored.com/lycored-nutrient-complex/.

Hermoni, K. L., & Raz, G. (2017). Tomato based supplement protects skin from UV damage and photo-aging processes. FASEB, 31(S1), 635.4. https://doi.org/10.1096/fasebj.31.1_supplement.635.4.

Aust O, Stahl W, Sies H, Tronnier H, Heinrich U. Supplementation with tomato-based products increases lycopene, phytofluene, and phytoene levels in human serum and protects against UV-light-induced erythema. Int J Vitam Nutr Res. Jan. 2005;75(1):54-60. doi: 10.1024/0300-9831.75.1.54. PMID: 15830922.

U.S . Food and Drug Administration, Center for Food Safety and Applied Nutrition, Office of Food Additive Safety, Division of Biotechnology and GRAS Notice Review. (2017). GRAS Notice for Tomato Fruit Powder. U.S. Food and Drug Adminstration.

Park M, Han J, Lee CS, Soo BH, Lim KM, Ha H. Carnosic acid, a phenolic diterpene from rosemary, prevents UV-induced expression of matrix metalloproteinases in human skin fibroblasts and keratinocytes. Exp Dermatol. May 2013;22(5):336-41. doi: 10.1111/exd. 12138. PMID: 23614740.

Groten K, Marini A, Grether-Beck S, Jaenicke T, Ibbotson SH, Moseley H, Ferguson J, Krutmann J. Tomato Phytonutrients Balance UV Response: Results from a Double-Blind, Randomized, Placebo-Controlled Study. Skin Pharmacol Physiol. 2019;32(2):101-108. doi: 10.1159/000497104. Epub Mar. 5, 2019. PMID: 30836363; PMCID: PMC6482986.

Havas F, Krispin S, Meléndez-Martínez AJ, von Oppen-Bezalel L. Preliminary Data on the Safety of Phytoene- and Phytofluene-Rich Products for Human Use including Topical Application. J Toxicol. Apr. 15, 2018;2018:5475784. doi: 10.1155/2018/5475784. PMID: 29849613; PMCID: PMC5925131.

(Continued)

*Primary Examiner* — Andrew S Rosenthal
(74) *Attorney, Agent, or Firm* — The Roy Gross Law Firm, LLC; Roy D. Gross

(57) ABSTRACT

The invention is directed to compositions comprising lycopene and to methods of using the same, such as for improving one or more skin parameters. e.g., prevention or treatment of various skin-related conditions caused by ultraviolet radiation.

15 Claims, 7 Drawing Sheets

(56) References Cited

OTHER PUBLICATIONS

Sies H, Stahl W. Nutritional protection against skin damage from sunlight. Annu Rev Nutr. 2004;24:173-200. doi: 10.1146/annurev.nutr.24.012003.132320. PMID: 15189118.

Stahl W, van den Berg H, Arthur J, Bast A, Dainty J, Faulks RM, Gärtner C, Haenen G, Hollman P, Holst B, Kelly FJ, Polidori MC, Rice-Evans C, Southon S, van Vliet T, Viña-Ribes J, Williamson G, Astley SB. Bioavailability and metabolism. Mol Aspects Med. Feb.-Jun. 2002;23(1-3):39-100. doi: 10.1016/s0098-2997(02)00016-x. PMID: 12079770.

Afaq F, Mukhtar H. Photochemoprevention by botanical antioxidants. Skin Pharmacol Appl Skin Physiol. Sep.-Oct. 2002;15(5):297-306. doi: 10.1159/000064533. PMID: 12239423.

Grether-Beck S, Marini A, Jaenicke T, Stahl W, Krutmann J. Molecular evidence that oral supplementation with lycopene or lutein protects human skin against ultraviolet radiation: results from a double-blinded, placebo-controlled, crossover study. Br J Dermatol. May 2017;176(5):1231-1240. doi: 10.1111/bjd.15080. Epub Mar. 15, 2017. PMID: 27662341.

Calniquer G, Khanin M, Ovadia H, Linnewiel-Hermoni K, Stepensky D, Trachtenberg A, Sedlov T, Braverman O, Levy J, Sharoni Y. Combined Effects of Carotenoids and Polyphenols in Balancing the Response of Skin Cells to UV Irradiation. Molecules. Mar. 30, 2021;26(7):1931. doi: 10.3390/molecules26071931. PMID: 33808148; PMCID: PMC8036680.

International search report for PCT/IL2019/050833 dated Sep. 26, 2019.

Written opinion for PCT/IL2019/050833 dated Sep. 26, 2019.

\* cited by examiner

LYCOPENE COMPOSITIONS AND METHODS FOR PROTECTING SKIN AGAINST ULTRAVIOLET RADIATION

CROSS REFERENCE TO RELATED APPLICATIONS

This application is a divisional of application Ser. No. 17/262,198, filed Jan. 21, 2021, which is a national phase of PCT Patent Application PCT/IL2019/050833, filed Jul. 23, 2019, which claims the benefit of priority of U.S. Provisional Patent Application No. 62/701,899, filed Jul. 23, 2018. The contents of the above referenced applications are incorporated herein by reference in its entirety.

FIELD OF INVENTION

This invention is directed to; inter alia, compositions comprising lycopene. More specifically, the present invention provides a composition comprising lycopene, which may be used, inter alia, in cosmetic compositions, ingestible skin care, treating skin-related conditions caused by ultraviolet radiation, or a combination thereof.

BACKGROUND OF THE INVENTION

It is well established that prolonged exposure to sun has damaging effects on the skin. Particularly, the ultraviolet (UV) radiation from the sun is known to cause erythema of the skin, sunburn and skin cancer. Protection of the skin from UV radiation can be achieved by protective attire as well as by protection in the form of topical compositions of various protective ingredients. A particular group of protective compositions are intended for oral administration. Oral compositions contain active ingredients which are delivered to the skin via an internal transport mechanism and thus protect the skin from UV radiation damage. A particular group of active ingredients which are suitable for use with said oral compositions are carotenoids. U.S. Pat. No. 3,920,834 describes the use of a mixture of carotenoids wherein canthaxanthin is the primary carotenoid in the composition. However, the use of canthaxanthin is known to be limited due to adverse effects it may have on pigmentation. U.S. Pat. No. 5,290,605 describes food-stuff and beverages intended for providing protection to the skin against UV sun radiation. Said foodstuff and beverages comprising carotenoids as well as ascorbic acid, tocopherols, coenzyme Q10 and reduced glutathione. U.S. Pat. No. 6,110,478 further patent describes a composition for protecting skin against UV radiation and the harmful effects thereof, wherein the composition contains a pro-vitamin A carotenoid and lycopene. The use of such a composition is limited by the negative effect pro-vitamin A carotenoids may have on the subject's health at certain dosage levels. An excess of vitamin A, which is produced in the body from pro-vitamin A carotenoids, was found to have adverse effects on health. Stahl et al ("Dietary Tomato Paste Protects against Ultraviolet Light-induced Erythema in Humans", Biochemical and Molecular Action of Nutrients, Research Communication, (2001) 1449-1451) have shown the protective effect of tomato paste which is known to contain inter alia lycopene, beta-carotene and tocopherol, against UV light-induced erythema. However, Stahl has reported a problem in achieving desired carotenoid serum levels, suggesting poor bioavailability.

Accordingly, there is a long felt need to develop a composition for protecting skin against UV radiation, as well as improving other skin parameters, which is suitable for oral administration and is safe at a wide range of dosages.

SUMMARY OF THE INVENTION

The present invention is directed, in some embodiments, to compositions comprising lycopene and use thereof, such as in oral formulations. Further provided are methods for their use in prevention or treatment of different skin conditions, or improving skin appearance or health. In some embodiments skin conditions are caused by ultraviolet radiation.

According to one aspect, there is provided a composition comprising (a) lycopene; (b) phytoene and phytofluene; and (c) carnosic acid, wherein the weight ratio of (a) to (b) is from 1:0.05 to 1:0.9.

According to another aspect, there is provided a method for improving one or more skin parameters in a subject in need thereof, comprising the step of administering to the subject a therapeutically effective amount of the herein disclosed composition, thereby improving one or more skin parameters in the subject.

In some embodiments, the weight ratio of lycopene and carnosic acid is from 1:0.05 to 1:0.9.

In some embodiments, the composition further comprises tocopherol.

In some embodiments, the weight ratio of lycopene and tocopherol is from 1:0.05 to 1:0.9.

In some embodiments, the composition further comprises beta-carotene.

In some embodiments, the weight ratio of lycopene and beta-carotene is from. 1:0.005 to 1:0.5.

In some embodiments, the composition is an oral composition.

In some embodiments, the composition further comprises a nutraceutical, a cosmeceutical, or a pharmaceutical acceptable excipient.

In some embodiments, the composition is for use in improving one or more skin parameters.

In some embodiments, the one or more skin parameters are selected from the group consisting of: face lines/wrinkles, mean skin carotenoid level, skin luminosity, skin radiance, and ultraviolet radiation (UV)-induced damage.

In some embodiments, the composition is a cosmeceutical composition.

In some embodiments, the composition is an anti-wrinkles composition.

In some embodiments, the method comprises a step of determining the level of a carotenoid in the skin of a subject, wherein a reduced level of said carotenoid in the skin of the subject compared to a control baseline is indicative of the subject is suitable for treatment using the herein disclosed composition.

In some embodiments, the subject is afflicted with a reduced level of a carotenoid.

In some embodiments, the skin is the palm skin.

In some embodiments, improving UV-induced damage in a subject comprises preventing or treating a skin-related condition caused by UV radiation in the subject.

In some embodiments, treating comprises inhibiting the production of TNF-alpha, IL-6, erythema reduction, or any combination thereof, in the subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
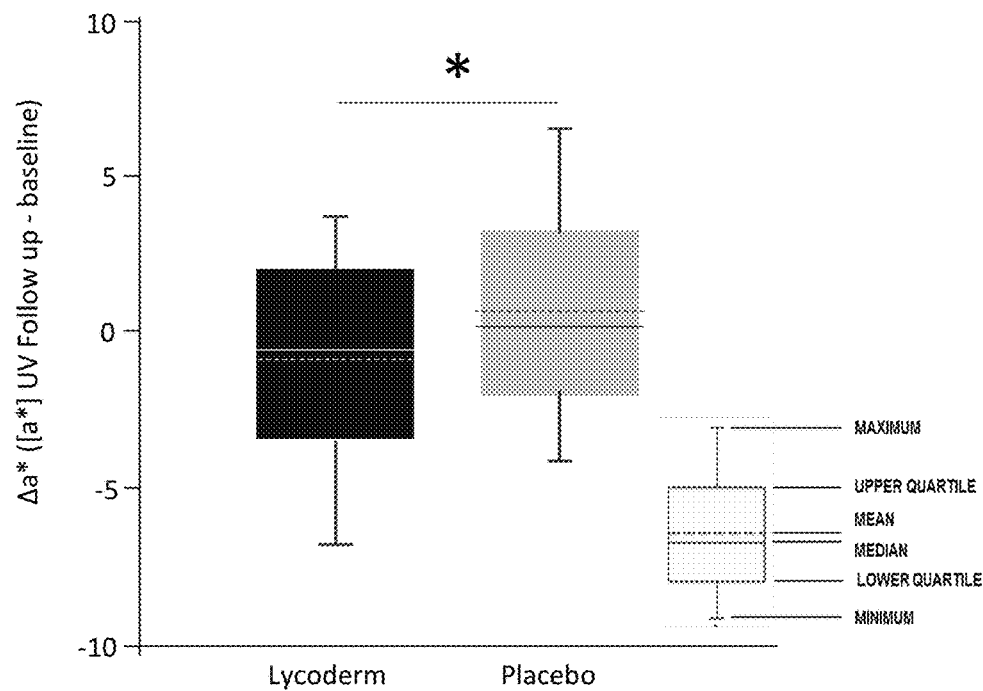
FIG. 1 is a bar graph showing the level changes in UV-induced erythema on subjects after treatment with formulation 1 of the present invention and treatment with placebo. Asterisk represents P value=0.019.

In one embodiment, the present invention provides a composition comprising lycopene, phytoene and phytofluene, and carnosic acid. In one embodiment, the present invention provides a composition comprising lycopene, phytoene, phytofluene, carnosic acid, tocopherol (e.g., vitamin E), and beta-carotene.

In another embodiment, lycopene is a natural lycopene extracted from a fruit or a vegetable. In another embodiment, lycopene is lycopene extracted from a tomato plant. In another embodiment, lycopene is lycopene extracted from a tomato fruit. In another embodiment, tomato lycopene is a tomato extract enriched for lycopene. In another embodiment, tomato lycopene is a lycopene-rich tomato extract which is all-natural. In another embodiment, tomato lycopene is a tomato lycopene complex. In another embodiment, tomato lycopene complex comprises a complex of phytonutrients including phytoene, phytofluene, beta-carotene, tocopherols and phytosterols. In another embodiment, tomato lycopene is Lyc-O-Mato® (LycoRed Ltd., Be'er Sheva, Israel).

Suitable processes for preparing this extract and similar extracts are described in U.S. Pat. No. 5,837,311, the specification of which is incorporated herein by reference in its entirety. However, it is to be recognized that many other types of preparatory procedures may be used to obtain the composition from a variety of plant sources.

In another embodiment, a composition as described herein further comprises phytoene. In another embodiment, a composition as described herein further comprises phytofluene. In another embodiment, a composition as described herein further comprises beta-carotene. In another embodiment, a composition as described herein further comprises tocopherol. In another embodiment, a composition as described herein further comprises a combination of any two or more of: phytoene, phytofluene, beta-carotene and tocopherol. In another embodiment, phytoene, phytofluene, beta-carotene and tocopherol are of natural source. In another embodiment, phytoene, phytofluene, beta-carotene and tocopherol are derived from a tomato. In another embodiment, phytoene, phytofluene, beta-carotene, tocopherol, or any combination thereof is produced synthetically.

In some embodiment, the ingredients described herein are natural-extracted from a plant. In some embodiment, the any ingredient described herein is natural-extracted from a plant.

In another embodiment, the weight ratio of lycopene, and phytoene and phytofluene ranges from 1:0.05 to 1:0.9. In another embodiment, the weight ratio of lycopene, and phytoene and phytofluene ranges from 1:0.1 to 1:0.9. In another embodiment, the weight ratio of lycopene, and phytoene and phytofluene ranges from 1:0.4 to 1:0.9. In another embodiment, the weight ratio of lycopene, and phytoene and phytofluene ranges from 1:0.1 to 1:0.5. In another embodiment, the weight ratio of lycopene, and phytoene and phytofluene ranges from 1:0.3 to 1:0.5.

In another embodiment, a composition as described comprises lycopene at a concentration of at least 0.5% (w/w). In another embodiment, a composition as described comprises lycopene at a concentration of at least 0.9% (w/w). In another embodiment, a composition as described comprises lycopene at a concentration of at least 1% (w/w). In another embodiment, a composition as described comprises lycopene at a concentration of at least 1.5% (w/w).

In another embodiment, a composition as described comprises lycopene at a concentration of 0.5-0.8% (w/w). In another embodiment, a composition as described comprises lycopene at a concentration of 0.5-1.1% (w/w). In another embodiment, a composition as described comprises lycopene at a concentration of 0.5-1.6% (w/w). In another embodiment, a composition as described comprises lycopene at a concentration of 0.5-1.5% (w/w).

In another embodiment, a composition as described comprises phytoene and phytofluene at a concentration of at least 0.3% (w/w). In another embodiment, a composition as described comprises phytoene and phytofluene at a concentration of at least 0.4% (w/w). In another embodiment, a composition as described comprises phytoene and phytofluene at a concentration of at least 0.5% (w/w). In another embodiment, a composition as described comprises phytoene and phytofluene at a concentration of at least 0.6% (w/w). In another embodiment, a composition as described comprises phytoene and phytofluene at a concentration of at least 0.9% (w/w). In another embodiment, a composition as described comprises phytoene and phytofluene at a concentration of at least 1% (w/w). In another embodiment, a composition as described comprises phytoene and phytofluene at a concentration of at least 1.5% (w/w).

In another embodiment, a composition as described comprises phytoene and phytofluene at a concentration of 0.3-1% (w/w). In another embodiment, a composition as described comprises phytoene and phytofluene at a concentration of 0.3-1.1% (w/w). In another embodiment, a composition as described comprises phytoene and phytofluene at a concentration of 0.3-1.3% (w/w). In another embodiment, a composition as described comprises phytoene and phytofluene at a concentration of 0.3-1.5% (w/w).

In another embodiment, a composition as described comprises carnosic acid at a concentration of at least 0.05% (w/w). In another embodiment, a composition as described comprises carnosic acid at a concentration of at least 0.1% (w/w). In another embodiment, a composition as described comprises carnosic acid at a concentration of at least 0.2% (w/w). In another embodiment, a composition as described comprises carnosic acid at a concentration of at least 0.3% (w/w). In another embodiment, a composition as described comprises carnosic acid at a concentration of at least 0.4% (w/w). In another embodiment, a composition as described comprises carnosic acid at a concentration of at least 0.5% (w/w).

In another embodiment, a composition as described comprises carnosic acid at a concentration of 0.05-1.2% (w/w). In another embodiment, a composition as described comprises carnosic acid at a concentration of 0.05-1.0% (w/w). In another embodiment, a composition as described comprises carnosic acid at a concentration of 0.05-0.75% (w/w). In another embodiment, a composition as described comprises carnosic acid at a concentration of 0.05-0.5% (w/w).

In another embodiment, the weight ratio of lycopene and carnosic acid ranges from 1:0.05 to 1:0.9. In another embodiment, the weight ratio of lycopene and carnosic acid ranges from 1:0.1 to 1:0.9. In another embodiment, the weight ratio of lycopene and carnosic acid ranges from 1:0.4 to 1:0.9. In another embodiment, the weight ratio of lycopene and carnosic acid ranges from 1:0.1 to 1:0.5. In another embodiment, the weight ratio of lycopene and carnosic acid ranges from 1:0.3 to 1:0.5.

In another embodiment, the weight ratio (w/w) of lycopene and carnosic acid in a composition of the invention is from 1:0.1 to 1:1. In another embodiment, the weight ratio (w/w) of lycopene and carnosic acid in a composition of the invention is from 1:0.1 to 1:0.3. In another embodiment, the weight ratio (w/w) of lycopene and carnosic acid in a composition of the invention is from 1:0.1 to 1:0.4. In another embodiment, the weight ratio (w/w) of lycopene and carnosic acid in a composition of the invention is from 1:0.1 to 1:0.8. In another embodiment, the weight ratio (w/w) of lycopene and carnosic acid in a composition of the invention is from 1:0.2 to 1:0.4 In another embodiment, the weight ratio (w/w) of lycopene and carnosic acid in a composition of the invention is from 1:0.25 to 1:1. In another embodiment, the weight ratio (w/w) of lycopene and carnosic acid in a composition of the invention is from 1:0.3 to 1:1. In another embodiment, the weight ratio (w/w) of lycopene and carnosic acid in a composition of the invention is from 1:0.4 to 1:1. In another embodiment, the weight ratio (w/w) of lycopene and carnosic acid in a composition of the invention is from 1:0.5 to 1:1 In another embodiment, the weight ratio (w/w) of lycopene and carnosic acid in a composition of the invention is from 1:0.8 to 1:1.

In another embodiment, a composition as described comprises tocopherol, for example vitamin E at a concentration of at least 0.1% (w/w). In another embodiment, a composition as described comprises vitamin E at a concentration of at least 0.2% (w/w). In another embodiment, a composition as described comprises vitamin E at a concentration of at least 0.5% (w/w). In another embodiment, a composition as described comprises vitamin E at a concentration of at least 0.8% (w/w). In another embodiment, a composition as described comprises vitamin E at a concentration of at least 1% (w/w). In another embodiment, a composition as described comprises vitamin E at a concentration of at least 1.5% (w/w). In another embodiment, a composition as described comprises vitamin E at a concentration of at least 1.9% (w/w).

In another embodiment, a composition as described comprises tocopherol, for example vitamin E, at a concentration of 0.1-2.0% (w/w). In another embodiment, a composition as described comprises vitamin E at a concentration of 0.2-1.9% (w/w). In another embodiment, a composition as described comprises vitamin E at a concentration of 0.5-1.9% (w/w). In another embodiment, a composition as described comprises vitamin E at a concentration of 0.8-1.9% (w/w). In another embodiment, a composition as described comprises vitamin E at a concentration of 1-1.9% (w/w). In another embodiment, a composition as described comprises vitamin E at a concentration of 0.5-1.5% (w/w). In another embodiment, a composition as described comprises vitamin E at a concentration of 1.5-1.9% (w/w).

In another embodiment, the weight ratio of lycopene and vitamin E ranges from 1:0.05 to 1:0.9. In another embodiment, the weight ratio (w/w) of lycopene and vitamin E ranges from 1:0.1 to 1:0.9. In another embodiment, the weight ratio of lycopene and vitamin E ranges from 1:0.3 to 1:0.9. In another embodiment, the weight ratio of lycopene and vitamin E ranges from 1:0.4 to 1:0.9. In another embodiment, the weight ratio of lycopene and vitamin E ranges from 1:0.1 to 1:0.5. In another embodiment, the weight ratio of lycopene and vitamin E ranges from 1:0.3 to 1:0.5.

In another embodiment, a composition as described comprises beta-carotene at a concentration of at least 0.01% (w/w). In another embodiment, a composition as described comprises beta-carotene at a concentration of at least 0.05% (w/w). In another embodiment, a composition as described comprises beta-carotene at a concentration of at least 0.07% (w/w). In another embodiment, a composition as described comprises beta-carotene at a concentration of at least 0.1% (w/w). In another embodiment, a composition as described comprises beta-carotene at a concentration of at least 0.15% (w/w). In another embodiment, a composition as described comprises beta-carotene at a concentration of at least 0.19% (w/w).

In another embodiment, a composition as described comprises beta-carotene at a concentration of 0.01-0.2% (w/w). In another embodiment, a composition as described comprises beta-carotene at a concentration of 0.01-0.19% (w/w). In another embodiment, a composition as described comprises beta-carotene at a concentration of 0.02-0.18% (w/w). In another embodiment, a composition as described comprises beta-carotene at a concentration of 0.03-0.15% (w/w).

In another embodiment, the weight ratio (w/w) of lycopene and beta-carotene ranges from 1:0.005 to 1:0.9. In another embodiment, the weight ratio of lycopene and beta-carotene ranges from 1:0.01 to 1:0.9. In another embodiment, the weight ratio of lycopene and beta-carotene ranges from 1:0.05 to 1:0.9. In another embodiment, the weight ratio of lycopene and beta-carotene ranges from 1:0.1 to 1:0.9. In another embodiment, the weight ratio of lycopene and beta-carotene ranges from 1:0.3 to 1:0.9. In another embodiment, the weight ratio of lycopene and beta-carotene ranges from 1:0.4 to 1:0.9. In another embodiment, the weight ratio of lycopene and beta-carotene ranges from 1:0.1 to 1:0.5. In another embodiment, the weight ratio of lycopene and beta-carotene ranges from 1:0.3 to 1:0.5.

In another embodiment, a composition as described comprises from 2.5 to 30 mg lycopene. In another embodiment, a composition as described comprises 6 mg lycopene. In another embodiment, a composition as described comprises from 6 to 20 mg lycopene. In another embodiment, a composition as described comprises 7 mg lycopene. In another embodiment, a composition as described comprises from 7 to 10 mg lycopene. In another embodiment, a composition as described comprises from 5 to 15 mg lycopene.

In another embodiment, a composition as described comprises 0.5 mg to 10 mg carnosic acid. In another embodiment, a composition as described comprises 1 mg to 5 mg carnosic acid. In another embodiment, a composition as described comprises 2 mg carnosic acid. In another embodiment, a composition as described comprises 2 mg to 4 mg carnosic acid.

In one embodiment, "concentration" is concentration from the overall composition. In one embodiment, "concentration" of a certain ingredient is its w/w concentration from the overall composition.

The components of the above-disclosed compositions may be purified compounds, synthetic compounds or may be present in mixture with other components, for example in plant extracts such as rosemary extract (in the case of carnosic acid), or a tomato extract (such as Lyc-O-Mato® which is commercially available from LycoRed, Be'er Sheva, Israel—in the case of lycopene and other carotenoids). In some embodiments, carnosic acid is supplied as rosemary extract. In some embodiments, carnosic acid is obtained from a rosemary extract.

In some embodiments, a composition as described herein is an oral composition. In some embodiments, a composition as described herein further comprises a pharmaceutical or a nutraceutical acceptable excipient. In some embodiments, a composition as described herein is a cosmeceutical composition. In some embodiments, a composition as described herein further comprises a cosmeceutical acceptable excipient. In some embodiments, a composition as described herein is a nutraceutical composition. In some embodiments, a composition as described herein further comprises a nutraceutical acceptable excipient In some embodiments, a composition as described herein in an ingestible skin/beauty composition.

In some embodiments, the composition is an anti-wrinkles composition. In some embodiments, the composition reduces the number of wrinkles on a subject's skin and/or face. In some embodiments, the composition reduces the depth of wrinkles on a subject's skin and/or face. In some embodiments, the composition prevents or reduces the development of wrinkles on a subject's skin and/or face. In some embodiments, the composition induces or promotes the filing of existing wrinkles on a subject's skin and/or face. In some embodiments, the composition further comprises one or more active compounds, wherein the one or more active components have anti-wrinkles and/or anti-aging activity, e.g., skin filing, moisture retaining, skin thickening, and others, for example, hyaluronic acid or botulinum toxins. In some embodiments, a composition further comprising one or more active compounds, wherein the one or more active components have anti-wrinkles and/or anti-aging activity, e.g., skin filing, moisture retaining, skin thickening, and others, for example, hyaluronic acid or botulinum toxins, comprises lower doses of the one or more active compound compared to cases wherein each of the one or more active components is administered solely (i.e., not combined with the composition of the invention).

In some embodiments, the herein disclosed composition is for use in improving one or more skin parameters, wherein the one or more skin parameters are selected from: face lines/wrinkles, mean tissue carotenoid level, skin luminosity, skin radiance, and ultraviolet radiation (UV)-induced damage.

In some embodiments, a method for improving one or more skin parameters in a subject in need thereof, comprising the step of administering to the subject a therapeutically effective amount of the herein disclosed composition, is provided.

In some embodiments, the method comprises a step of determining the level of carotenoid in the skin of a subject. In some embodiments, the method comprises a step of determining the level of carotenoid in the palm skin of a subject. In some embodiments, a reduced level of the carotenoid in the skin and/or the palm skin of the subject compared to a control baseline is indicative of the subject is suitable for treatment using the herein disclosed composition.

In some embodiments, the term "control baseline" refers to the normal range of palm skin carotenoid level, or any value therebetween. The normal range of palm skin carotenoid level would be apparent to one of ordinary skill in the art. Methods for determining mean tissue carotenoid level are common, and a non-limiting example of which includes, but is not limited to biophotonic scanning, as exemplified hereinbelow.

As used herein, the term "carotenoid" encompasses lycopene, phytoene, phytofluene, or metabolites thereof.

In some embodiments, the subject has normal level of carotenoids in the skin and/or palm skin. In some embodiments, the subject is afflicted with a reduced level of carotenoids in the skin and/or palm skin.

In some embodiments, the one or more skin parameters are selected from: face skin lines/wrinkles, mean tissue carotenoid level, skin radiance, skin luminosity, and ultraviolet (UV)-induced damage.

As used herein, the term "UV" encompasses any wavelength of the UV range. In some embodiments, UV is UV radiation. In some embodiments, UV radiation is UVB radiation.

In some embodiments, the tissue comprises skin. In some embodiments, skin comprises the palm skin.

In some embodiments, improving UV-induced damage in a subject comprises preventing or treating a skin-related condition caused by UV radiation in the subject.

In another embodiment, the present invention provides that treating a subject afflicted with skin-related conditions caused by ultraviolet radiation is inhibiting the production of markers of skin damage and immune-modulatory cytokines. In another embodiment, the present invention provides that treating a subject afflicted with skin-related conditions caused by ultraviolet radiation is reduction of erythema formation.

In one embodiment, "skin-related conditions" refers to skin damage caused by exogenous factors such as exposure to ultraviolet radiation. In one embodiment, a skin condition is caused by an irritant. In one embodiment, a skin condition is caused by a chemical or any other toxic factor. In one embodiment, skin-related conditions include, without being limited thereto, skin thickness, sunburn cells, erythema, skin irritation, redness, dryness, stinging, skin peeling and detachment, acne-like skin eruptions, skin spots and skin color tone non-uniformity, infection and loss of fluids, or any combination thereof.

In another aspect, the present invention is directed to the use of a composition such as described herein for the manufacture of a medicament for the treatment of conditions responsive to inhibition of the production of: TNF-alpha, IL-6, IL-1, IL-10, MMP-1, HO-1, ICAM-1 or any combination thereof.

In some embodiments of the methods described hereinabove, the subject is a human subject. In some embodiments of the methods described hereinabove, the subject is a mammal. In some embodiments of the methods described hereinabove, the subject is a pet. In some embodiments of the methods described hereinabove, the subject is a farm animal. In some embodiments of the methods described hereinabove, the subject is a lab animal.

While in the above-disclosed methods, the therapeutic composition may be administered by any convenient means, in one embodiment the composition is administered in a pharmaceutical, a nutraceutical, nutritional, or oral dosage form.

In one embodiment, the composition of the present invention can be provided to the individual per-se. In one embodiment, the composition of the present invention can be provided to the individual as part of a further pharmaceutical composition or a nutraceutical composition where it is mixed with a pharmaceutically acceptable carrier.

In one embodiment, a "pharmaceutical composition", a "cosmeceutical composition" or a "nutraceutical composition" refers to a preparation of a composition as described herein with other chemical components such as physiologically suitable carriers and excipients. The purpose of a pharmaceutical composition, cosmeceutical composition, or a nutraceutical composition is to facilitate administration of the composition to an organism.

In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, the phrases "physiologically acceptable carrier" and "pharmaceutically acceptable carrier" which be interchangeably used refer to a carrier or a diluent that does not cause significant irritation to a mammal and does not abrogate the biological activity and properties of the administered composition. An adjuvant is included under these phrases.

In one embodiment, "excipient" refers to an inert substance added to a composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, PA, latest edition, which is incorporated herein by reference in its entirety.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In one embodiment, administration of the composition of the present invention is started before exposure to UV radiation. In one embodiment administration of the composition of the present invention is started 15 weeks before exposure to UV radiation. In one embodiment administration of the composition of the present invention is started 12 weeks before exposure to UV radiation. In one embodiment administration of the composition of the present invention is started 7 weeks before exposure to UV radiation. In one embodiment administration of the composition of the present invention is started 30 days before exposure to UV radiation. In one embodiment administration of the composition of the present invention is started 7 days before exposure to UV radiation. In one embodiment administration of the composition of the present invention is started 7 to 30 days before exposure to UV radiation and administration is continued during exposure to UV radiation.

In another embodiment, administration of the composition of the present invention is started 7 hours after exposure to UV radiation. In another embodiment, administration of the composition of the present invention is started 12 hours after exposure to UV radiation. In another embodiment, administration of the composition of the present invention is started 24 hours after exposure to UV radiation. In another embodiment, administration of the composition of the present invention is started 48 hours after exposure to UV radiation.

In one embodiment, administration of the composition of the present invention commences before the mean tissue carotenoid level is reduced below the control baseline. In one embodiment administration of the composition of the present invention commences 15 weeks before the mean tissue carotenoid level is reduced below the control baseline. In one embodiment administration of the composition of the present invention commences 12 weeks before the mean tissue carotenoid level is reduced below the control baseline. In one embodiment administration of the composition of the present invention commences 7 weeks before the mean tissue carotenoid level is reduced below the control baseline. In one embodiment administration of the composition of the present invention commences 30 days before the mean tissue carotenoid level is reduced below the control baseline. In one embodiment administration of the composition of the present invention commences 7 days before the mean tissue carotenoid level is reduced below the control baseline. In one embodiment administration of the composition of the present invention commences 7 to 30 days before the mean tissue carotenoid level is reduced below the control baseline and administration is continued while the mean tissue carotenoid level is reduced below the control baseline.

In another embodiment, the composition of the present invention is administrated at least 1 to 3 times daily. In another embodiment, the composition of the present invention is administrated once daily. In another embodiment, the composition of the present invention is administrated twice daily. In another embodiment, the composition of the present invention is administrated 3 times a day.

In another embodiment, reduction of erythema formation caused by UVB irradiation is observed after 3 weeks of administration of the composition of the present invention. In another embodiment, reduction of erythema formation caused by UVB irradiation is observed after 7 weeks of administration of the composition of the present invention. In another embodiment, reduction of erythema formation caused by UVB irradiation is observed after 12 weeks of administration of the composition of the present invention.

In another embodiment, prevention of erythema formation is observed after 3 weeks of administration of the composition of the present invention prior to UVB irradiation. In another embodiment, prevention of erythema formation is observed after 7 weeks of administration of the composition of the present invention prior to UVB irradiation. In another embodiment, prevention of erythema formation is observed after 12 weeks of administration of the composition of the present invention prior to UVB irradiation.

In another embodiment, reduction of cytokine levels is observed after 3 weeks of administration of the composition of the present invention. In another embodiment, reduction of cytokine levels is observed after 7 weeks of administration of the composition of the present invention. In another embodiment, reduction of cytokine levels is observed after 12 weeks of administration of the composition of the present invention.

In another embodiment, administration of the composition of the present invention for 3 weeks prior to UVB irradiation, results in a decrease in the levels of cytokines. In another embodiment, administration of the composition of the present invention for 7 weeks prior to UVB irradiation, results in a decrease in the levels of cytokines. In another embodiment, administration of the composition of the present invention for 12 weeks prior to UVB irradiation, results in a decrease in the levels of cytokines. Various embodiments of dosage ranges are contemplated by this invention. The dosage of the composition of the present invention, in one embodiment, is in the range of 0.5-2000 mg/day. In another embodiment, the dosage is in the range of 5-500 mg/day. In another embodiment, the dosage is in the range of 500-2000 mg/day. In another embodiment, the dosage is in the range of 0.1-10 mg/day. In another embodiment, the dosage is in the range of 50-500 mg/day. In another embodiment, the dosage is in the range of 5-4000 mg/day. In another embodiment, the dosage is in the range of 0.5-50 mg/day. In another embodiment, the dosage is in the range of 5-80 mg/day. In another embodiment, the dosage is in the range of 100-1000 mg/day. In another embodiment, the dosage is in the range of 1000-2000 mg/day. In another embodiment, the dosage is in the range of 200-600 mg/day. In another embodiment, the dosage is in the range of 400-1500 mg/day. In another embodiment, the dosage is in a range of 800-1500 mg/day. In another embodiment, the dosage is in the range of 500-2500 mg/day. In another embodiment, the dosage is in a range of 600-1200 mg/day. In another embodiment, the dosage is in the range of 1200-2400 mg/day. In another embodiment, the dosage is in the range of 40-60 mg/day. In another embodiment, the dosage is in a range of 2400-4000 mg/day. In another embodiment, the dosage is in a range of 450-1500 mg/day. In another embodiment, the dosage is in the range of 1500-2500 mg/day. In another embodiment, the dosage is in the range of 5-10 mg/day. In another embodiment, the dosage is in the range of 550-1500 mg/day. In another embodiment, "dosage" refers to the amount of an active ingredient or the combination of active ingredients of the invention. In another embodiment, "dosage" is not inclusive with respect to excipients. Aqueous solutions, buffers, vehicles, or any other inert substance.

In one embodiment, the dosage is 200 mg/day. In another embodiment, the dosage is 300 mg/day. In another embodiment, the dosage is 400 mg/day. In another embodiment, the dosage is 500 mg/day. In another embodiment, the dosage is 600 mg/day. In another embodiment, the dosage is 700 mg/day. In another embodiment, the dosage is 800 mg/day. In another embodiment, the dosage is 900 mg/day. In another embodiment, the dosage is 1000 mg/day.

Oral administration, in one embodiment, comprises a unit dosage form comprising tablets, capsules, lozenges, chewable tablets, suspensions, drinks, syrups, nectars, beverages, gummies, emulsions and the like. Such unit dosage forms comprise a safe and effective amount of the composition. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the active ingredient as known to one skilled in the art. In another embodiment, the composition is a drink or a beverage comprising a dosage which consists a combination of the active ingredients in a ratio or in an amount as described herein.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.012% to about 0.933% of the active ingredients, or in another embodiment, from about 0.033% to about 0.7%.

In some embodiments, pharmaceutical compositions for use in the methods of this invention comprise solutions or emulsions, which in some embodiments are aqueous solutions or emulsions comprising a safe and effective amount of the composition of the present invention and optionally, other compounds. In some embodiments, the compositions comprise from about 0.01% to about 10.0% w/v or w/w of a combination of active ingredients as described herein.

Further, in another embodiment, the compositions are administered topically to body surfaces, and are thus formulated in a form suitable for topical administration. Suitable topical formulations include gels, ointments, creams, lotions, drops and the like. For topical administration, the composition of the present invention is combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcysteine, sodium metabisulfite and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, compositions include aqueous solutions of the active preparation in water-soluble form. Additionally, suspensions of the active ingredients, in some embodiments, are prepared as appropriate oily or water-based suspensions. Suitable lipophilic solvents or vehicles include, in some embodiments, fatty oils such as sesame oil, or synthetic fatty acid esters such as ethyl oleate, triglycerides or liposomes. Aqueous suspensions contain, in some embodiments, substances, which increase the viscosity of the suspension, such as sodium carboxymethyl cellulose, sorbitol or dextran. In another embodiment, the suspension also contains suitable stabilizers or agents which increase the solubility of the active ingredients to allow for the preparation of highly concentrated solutions.

In some embodiments, compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

Some examples of substances which can serve as nutraceutical or pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of Theobroma; polyols such as propylene glycol, glycerin, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a nutraceutical or a pharmaceutically-acceptable carrier to be used in conjunction with the compound is basically determined by the way the compound is to be administered. If the subject compound is to be injected, in one embodiment, the nutraceutical or pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material, the compositions of the invention, into or onto particulate preparations of polymeric compounds such as polylactic acid, polglycolic acid, hydrogels, etc, or onto liposomes, microemulsions, micelles, unilamellar or multi-lamellar vesicles, erythrocyte ghosts, or spheroplasts.) Such compositions will influence the physical state, solubility, stability, rate of in vivo release, and rate of in vivo clearance. Also comprehended by the invention are particulate compositions coated with polymers (e.g. poloxamers or poloxamines).

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the composition described herein can be determined by standard nutraceutical or pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is affected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical or nutraceutical carrier are also be prepared, placed in an appropriate container, and labeled for treatment of an indicated condition.

In one embodiment, compositions of the present invention are presented in a pack or dispenser device, such as an FDA approved kit, which contain one or more unit dosage forms containing the composition. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of nutraceuticals or pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein, and the laboratory procedures utilized in the present invention include chemical, molecular, biochemical, and cell biology techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); "Cell Biology: A Laboratory Handbook", Volumes I-III Cellis, J. E., ed. (1994); The Organic Chemistry of Biological Pathways by John McMurry and Tadhg Begley (Roberts and Company, 2005); Organic Chemistry of Enzyme-Catalyzed Reactions by Richard Silverman (Academic Press, 2002); Organic Chemistry (6th Edition) by Leroy "Skip" G Wade;

Organic Chemistry by T. W. Graham Solomons and, Craig Fryhle.

Example 1

Preparation of Lycopene Composition

The lycopene used throughout the Examples is natural Tomato lycopene by Lycored®.
Formulation 1: Each capsule (Lyc-044) contained:
Lycopene 8.2 mg
Vitamin E 2.9 mg
Phytofluene and phytoene 3.00 mg
Beta-carotene 0.46 mg
Carnosic Acid 2 mg
In soft gel capsules which were prepared according to standard procedures known to the skilled artisan.

Example 2

Effect of Lycopene Composition in Protection of Healthy Skin from UV-Induced Photo-Oxidative Damage Methodology
A multicentre, double blind, placebo controlled parallel group clinical biostudy. After a 5-week run-in period, during which the intake of lycopene-rich foods and antioxidant supplements was restricted, subjects were randomized to receive formulation 1 soft gel capsules (Lyc-044) or identically appearing medium chain triglycerides soft gel capsules as placebo, twice daily for 12 weeks.
Number of Subjects (Planned and Analysed)
145 subjects completed the study and were analysed.
Diagnosis and Main Criteria for Inclusion
Healthy males and females, 20 to 55 years of age, with Fitzpatrick skin type I or II, BMI≤30 kg/m$^2$ and healthy eating habits.
Test Product, Dose and Mode of Administration
Formulation 1 soft gel capsules administered orally twice daily.
Reference Therapy, Dose and Mode of Administration
Placebo administered orally twice daily.
Duration of Treatment
12 weeks
Protection Against Erythema Measured by Chromametry
Chromametry is a method of measuring skin color using a chromameter. The color of the skin is measured using a L\*a\*b\* scale, where L\* reflects the luminance of a color on a gray scale, a\* reflects redness versus greenness, and b\* reflects blueness versus yellowness.

The subjects were tested for the protection from UV irradiation induced erythema. Each subject was UV irradiated on an area of his skin and the development of erythema was measured 24 hours after the irradiation.

For this analysis, Δa\* was defined as the difference between erythema development levels at 24 hours after UV irradiation before supplementation and erythema development levels at 24 hours after UV irradiation after supplementation. A statistically significant change in erythema formation was observed between the formulation 1 and placebo groups. Data is summarised in FIG. 1.

Conclusions

Supplementation for 12 weeks with formulation 1 significantly reduced erythema formation in response to UVB irradiation.

Cytokine Levels

Mean IL-1alpha, IL-6, IL-10 and TNF-alpha levels were assessed by polymerase chain reaction (PCR). The subjects participating in the clinical study were assayed for the levels of IL-1alpha, IL-6, IL-10 and TNF-alpha. Samples were obtained after UVB irradiation prior to randomization and after UVB irradiation done after 12 weeks of treatment with formulation 1 or placebo.

IL-1 alpha expression is upregulated upon UVB irradiation. The IL10 exerts profound immunosuppressive activities and is upregulated in response to UV irradiation in human skin. Keratinocytes produce and release IL6 upon UVB irradiation in human skin leading to increased plasma levels. The proinflammatory TNF-alpha is released in keratinocytes upon UVB irradiation.

Figure 2:
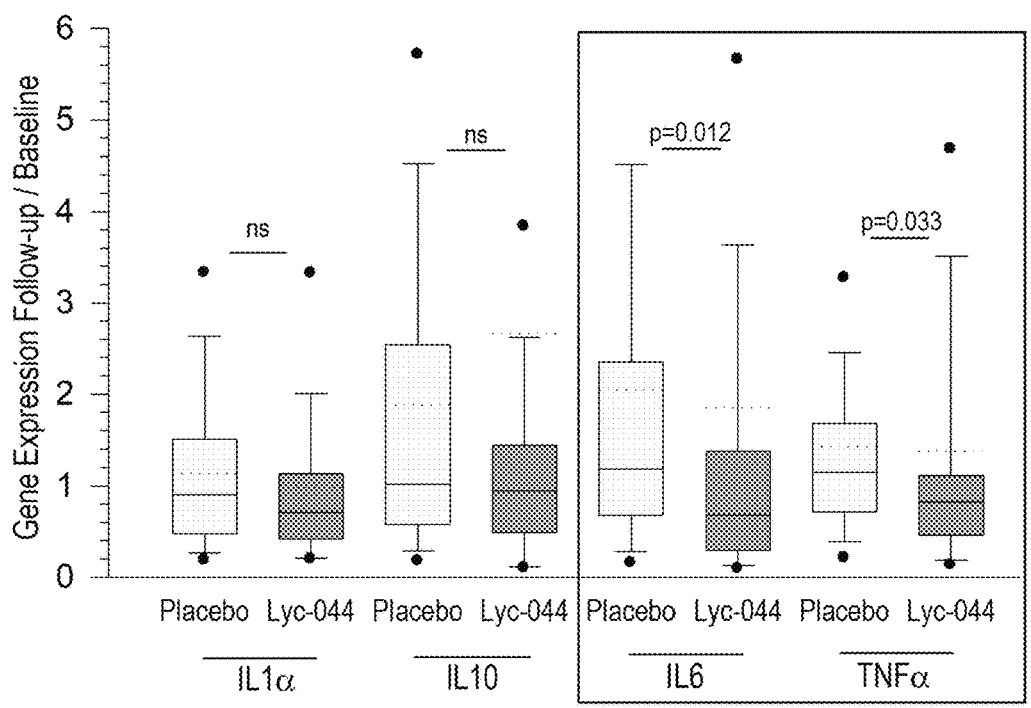
FIG. 2 is a bar graph showing the level changes in UV-induced gene expression on subjects after treatment with formulation 1 of the present invention and treatment with placebo.

FIG. 2 shows the changes in cytokine levels measured at baseline and follow-up.

Conclusions

Analysis of cytokine mRNAs from skin biopsies showed statistically significant differences between treatment groups in IL-6 and TNF-alpha: both these cytokines showed lower levels following supplementation and UVB irradiation, while in the placebo group, under the same conditions their levels increased. IL-10 and IL-1α levels in response to UVB irradiation did not differ between the formulation 1 supplementation and the placebo groups, respectively. Formulation 1 significantly decreased UVB-induced IL6 and TNF-alpha expression.

Example 3

Lycopene, Phytofluene and Phytoene Levels in the Serum of the Subjects

Methodology Compliance was measured by the increase in lycopene, phytofluene and phytoene levels during the study.

Figure 3A:
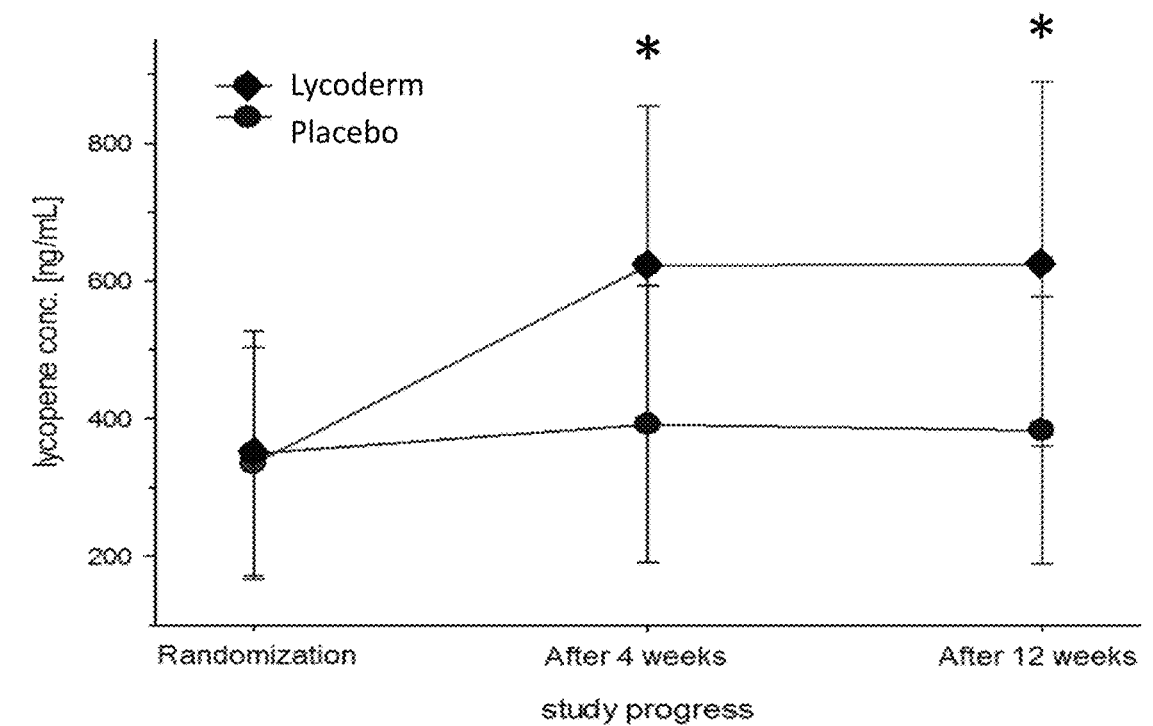
FIGS. 3A-3C are graphs showing the concentration of Lycopene (3A), Phytofluene (3B), and Phytoene (3C) during the study.
Figure 3B:
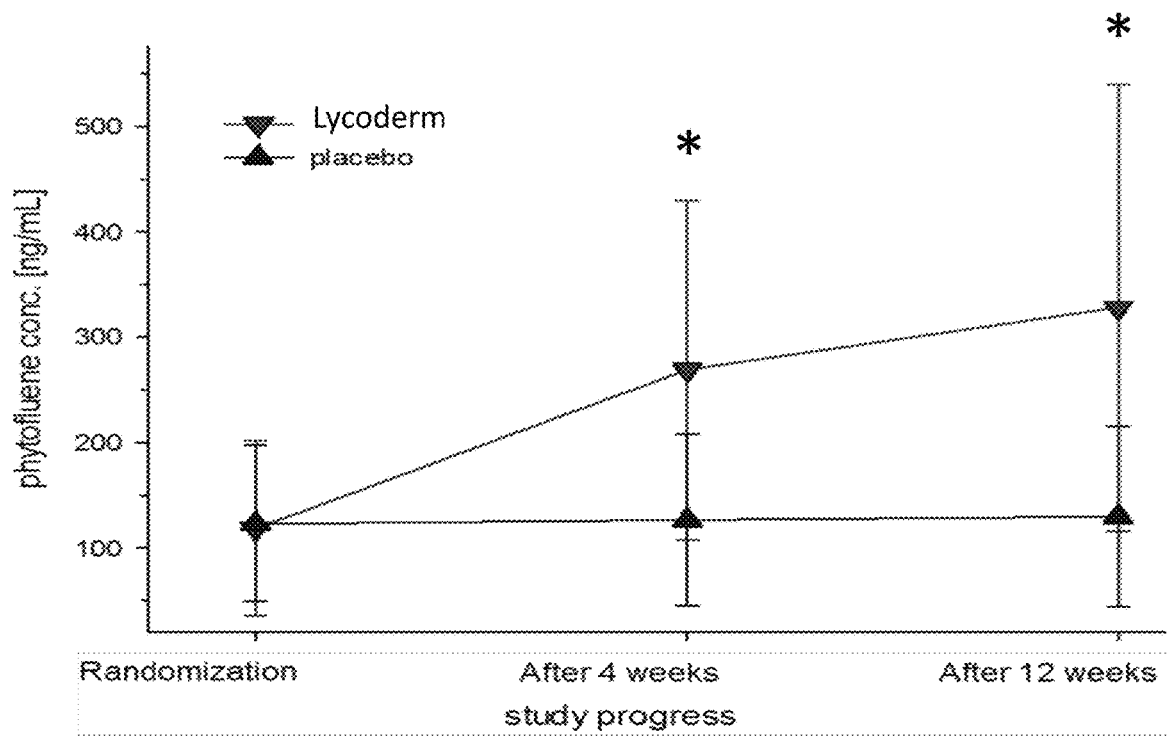
Figure 3C:
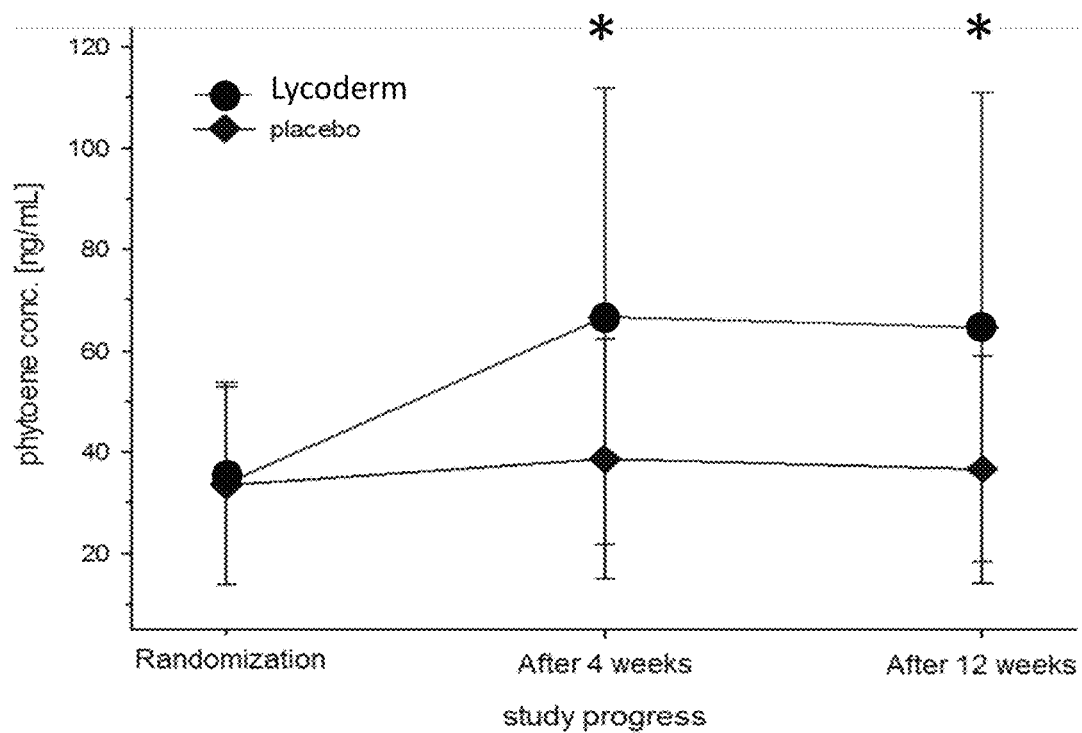

At the randomization visit (prior to receiving supplementation), mean lycopene, phytofluene and phytoene levels in the serum of the subjects of the Lyc-044 and placebo groups were similar. A statistically significant increase in mean lycopene, phytofluene and phytoene levels was observed after 4 weeks of treatment and at the end of the study in the Lyc-044 group compared to placebo (FIG. 3).

Example 4

Combination of Lycopene and Polyphenols Synergistically Inhibit UVB-Induced IL-6 Release Methodology
Cell culture and Treatment HaCaT keratinocyte cells were purchased from American Type Culture Collection (Manassas, VA, USA). The cells were grown in DMEM medium supplemented with penicillin (100 U/ml), streptomycin (0.1 mg/ml), Glutamine (2 mM), and 10% FCS (fetal calf serum). KERTr keratinocytes and normal human dermal fibroblasts (NHDF) were purchased from PromoCell GmbH (Heidelberg, Germany). KERTr cells were grown in keratinocytes serum free medium (Gibco) supplemented with bovine pituitary extract and EGF. NHDF cells were grown in fibroblast growth medium 2 (PromoCell) according to the manufacturer's instructions.

Measurement of IL-6 Levels

HaCaT cells were seeded in 24 well plates (120,000 cells/well) in DMEM medium supplemented with 10% FCS. The medium was changed to 3% FCS containing the different dietary compounds at the indicated concentrations. A day later medium was replaced with PBS (phosphate buffer saline) and the cells were irradiated with a UVB lamp (Ultra-Violet Products, Ltd., Upland, CA, 302 nm). The intensity of irradiation was measured with VLX-3W (VilberLourmat Deutschland GmbH, Eberhardzell, Germany). The PBS was replaced with medium containing 3% FCS plus the test compounds and the medium was collected after 6 h. IL-6 in medium was measured using Human IL-6 ELISA MAX™ Deluxe kit (Biolegend, San Diego, CA).

Conclusions

Figure 4:
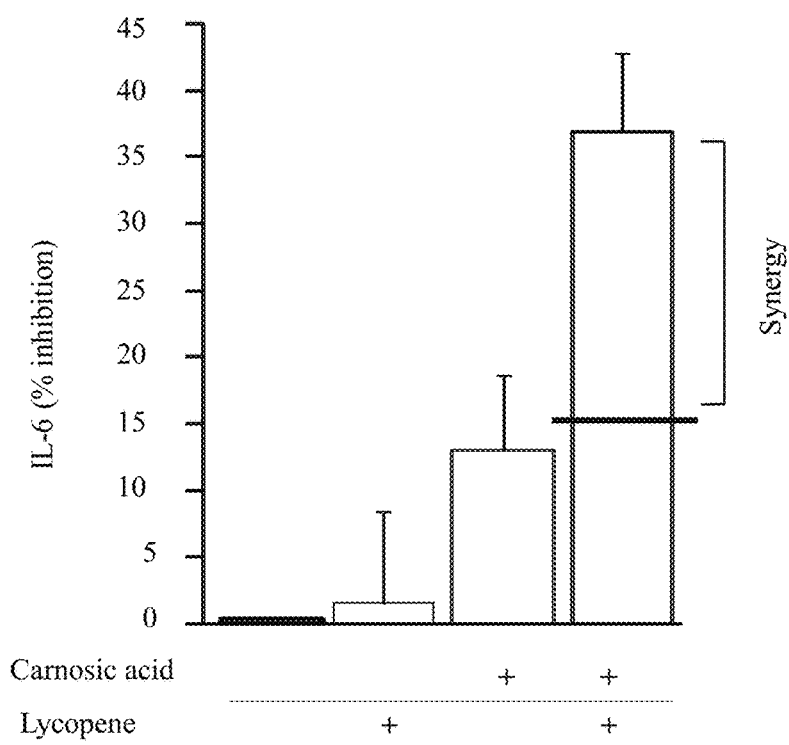
FIG. 4 is a bar graph showing the synergy between carnosic acid and lycopene in the inhibition of UVB-induced IL-6 release.

The combination of lycopene and carnosic acid inhibited synergistically UVB-induced IL-6 release (FIG. 4).

Figure 5A:
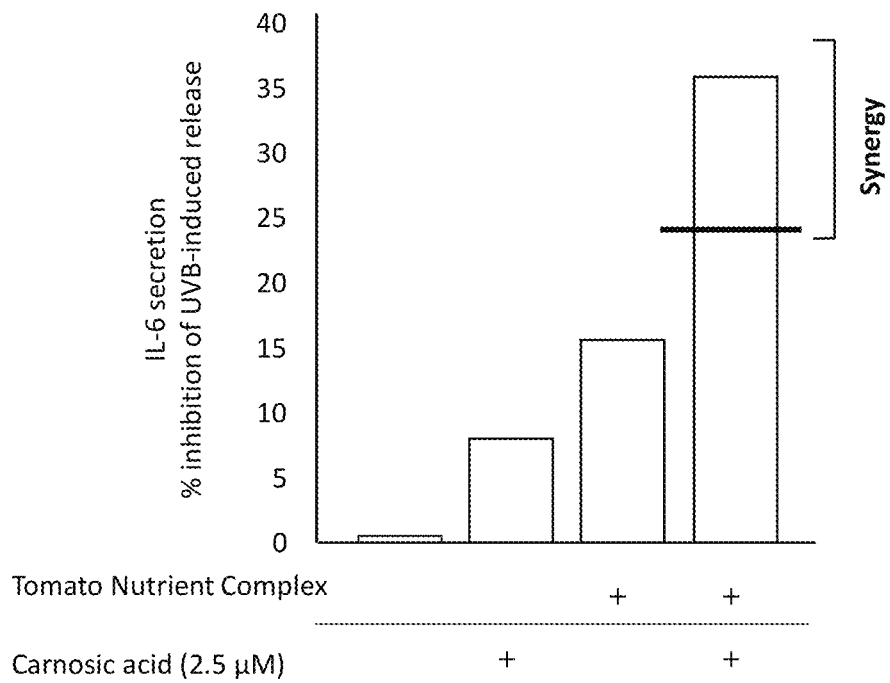
FIGS. 5A-5B are bar graphs showing the synergy between Lycored tomato nutrient complex and carnosic acid in the inhibition of UVB-induced IL-6 release. Ratios of Lycopene to Carnosic acid of 1:0.3 (w/w; 5A), and 1:0.6 (w/w; 5B) are shown.
Figure 5B:
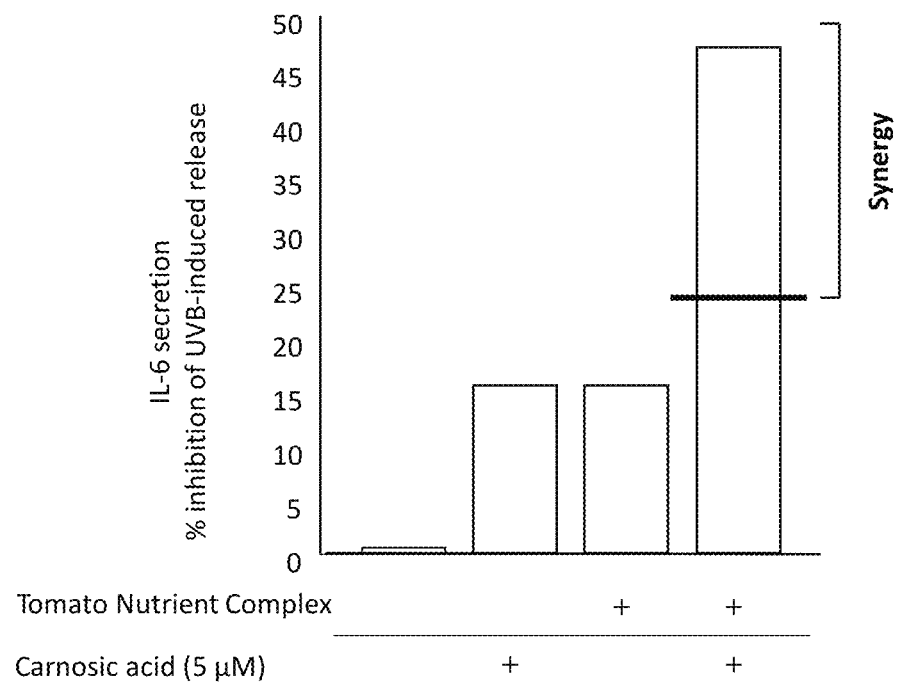

The combination of Lycored tomato nutrient complex with carnosic acid, inhibit IL-6 release synergistically from a ratio of 1:0.6 to 1:0.1 respectively (FIG. 5).

Example 5

Synergistic Activation of the Antioxidant Response Element (EpRE/ARE) Transcription System in Dermal Cells by Phytonutrient Combinations Methodology
Cell Culture and Treatment HaCaT keratinocyte cells were purchased from American Type Culture Collection (Manassas, VA, USA). The cells were grown in DMEM medium supplemented with penicillin (100 U/ml), streptomycin (0.1 mg/ml), Glutamin (2 mM), and 10% FCS. KERTr keratinocytes and normal human dermal fibroblasts (NHDF) were purchased from PromoCell GmbH (Heidelberg, Germany). KERTr cells were grown in keratinocytes serum free medium (Gibco) supplemented with bovine pituitary extract and EGF. NHDF cells were grown in fibroblast growth medium 2 (PromoCell) according to the manufacturer's instructions.

Transient Transfection and Reporter Gene Assay

Cells were transfected using jetPEI reagent (Polyplus Transfection, Illkrich, France) in 24 well plates. HaCaT cells (80,000 cells per well) were transfected with 0.2 μg NFkB-SEAP reporter construct and 0.05 μg normalizing plasmid. The ratio of DNA to jetPEI was 1:5. KERTr keratinocytes and NHDF fibroblasts were transfected with 0.2 μg 4×ARE reporter construct and 0.1 μg normalizing plasmid. Cells were seeded in culture media containing 3% FCS. On the next day, cells were rinsed once with the appropriate culture medium followed by addition of 0.45 ml of medium and 50 µl of DNA mixed with jetPEI. Cells were then incubated for 4-6 h at 37° C. Medium was replaced with one supplemented with 3% FCS plus the test compounds, and cells were incubated for additional 16-20 h.

ARE reporter activity was measured in cell extracts and normalized to renilla luciferase using the Dual Luciferase Reporter Assay System, (Promega, Madison, WI) according to the manufacturer's instructions. For NFkB reporter activity measurements, secreted alkaline phosphatase (SEAP) activity was measured in the culture media using Great Escape™ SEAP Chemiluminescence kit, (Clontech, Mountain View, CA) according to the manufacturer's instructions. Luciferase activity was measured in cell extracts by Luc assay kit (Promega, Madison, WI) and was used to normalize the results. All luminescence measurements were performed in Turner Biosystems Luminometer (Sunnyvale, CA). Of note, in different experiments transfection level as well as other parameters like cell batch and passage were variable. In combination experiments, the comparison between the different compounds in the same experiment were reproducible, however, basal reporter activity as well as the fold induction varied between experiments.

Conclusions

The effect of Tomato Nutrient Complex containing lycopene and rosemary extract containing Carnosic acid on the activation of the EpRE/ARE transcription system in skin epidermal keratinocytes and dermal fibroblasts was evaluated.

Figure 6A:
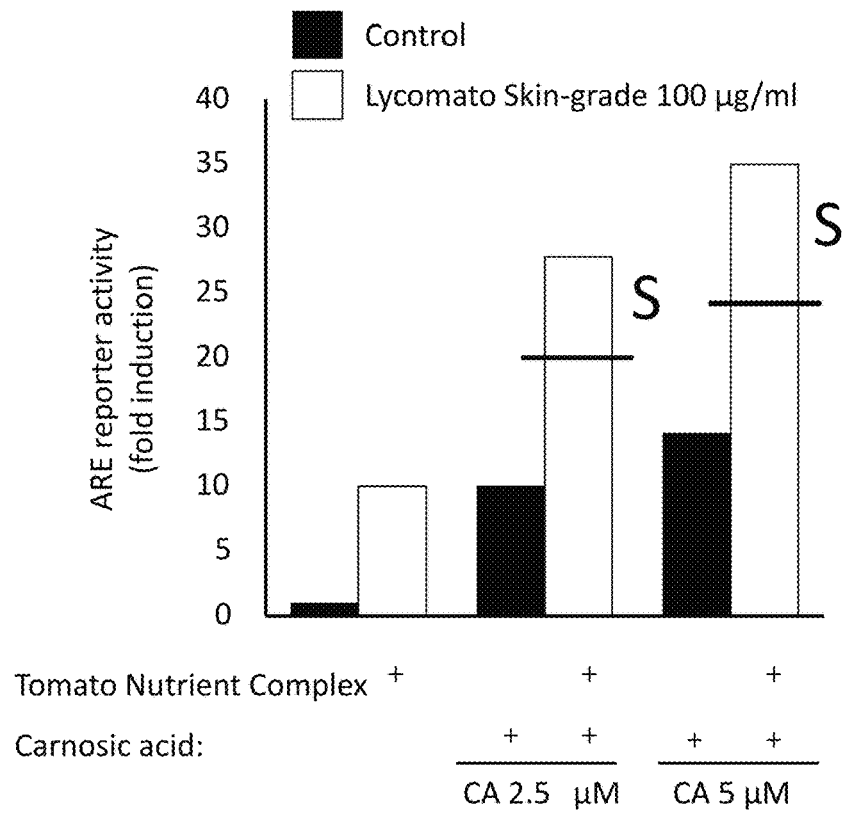
FIGS. 6A-6B are bar graphs showing the synergistic induction of the antioxidant response element (EpRE/ARE) reporter activity in epidermal keratinocytes by combinations of Tomato Nutrient Complex with Carnosic acid (6A) or Rosemary extract (6B) and Lycoderm preparation (comprising Nutrient Complex and the Rosemary extract combined). Ratios of Lycopene to Carnosic acid of 1:0.14 (i.e., CA 2.5 µM), and 1:0.27 (CA 5 µM) are shown. "S"—Synergy.
Figure 6B:
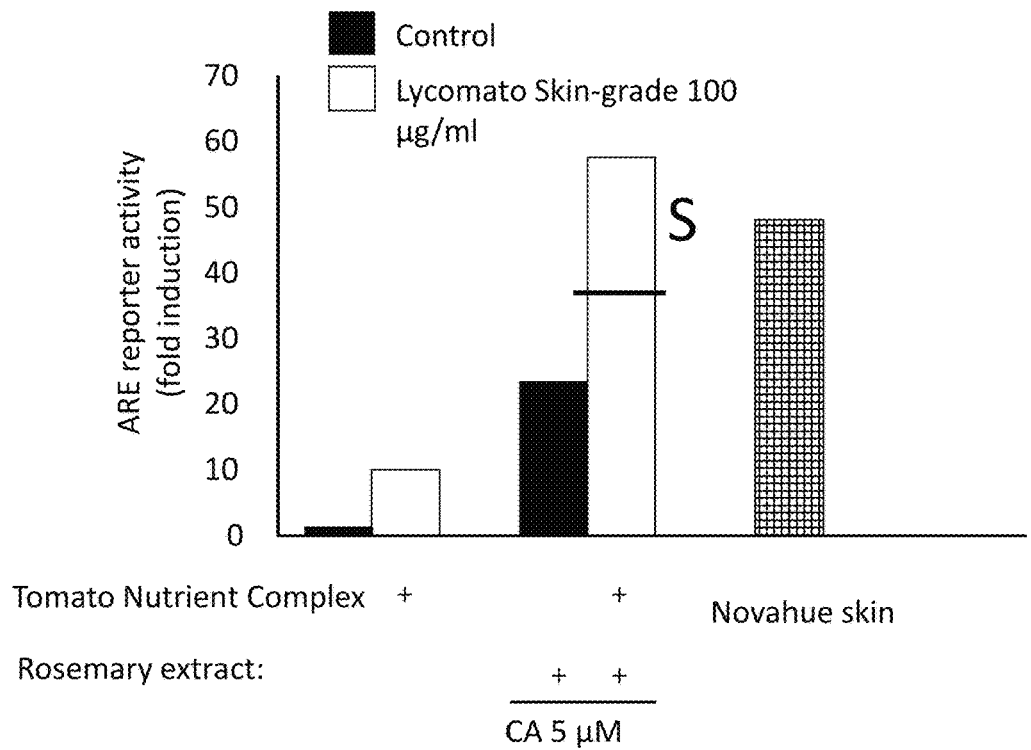

Activation of EpRE/ARE transcription system was measured in KERTr keratinocytes using a reporter gene assay as described above. Tomato Nutrient Complex containing all tomato phytonutrients such as lycopene phytoene and phytofluene, beta carotene, tocopherols and phytosterols was dissolved to provide a final concentration of 10 µM lycopene. It was combined with either purified Carnosic acid or with rosemary extract containing Carnosic acid. Both combinations produced synergistic activation of the EpRE/ARE reporter activity (FIGS. 6A-B).

Figure 7A:
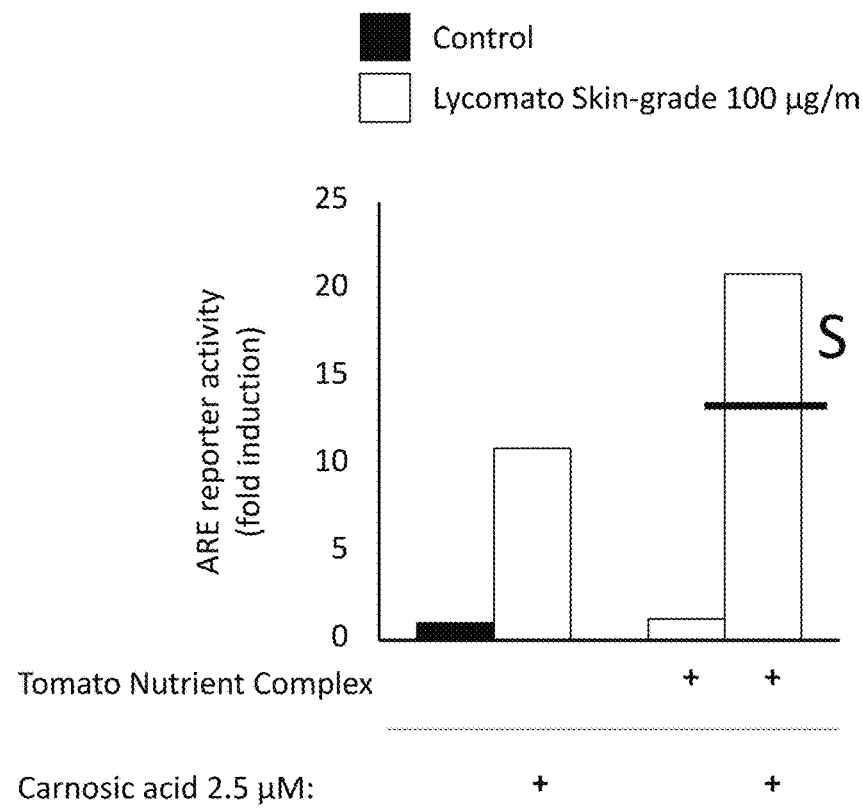
FIGS. 7A-7B are bar graphs showing the synergistic induction of EpRE/ARE reporter activity in dermal fibroblasts by combinations of Tomato Nutrient Complex and Carnosic acid. Ratios of Lycopene to Carnosic acid of 1:0.14 (i.e., CA 2.5 µM; 7A), and 1:0.27 (CA 5 µM; 7B) are shown. "S"—Synergy.
Figure 7B:
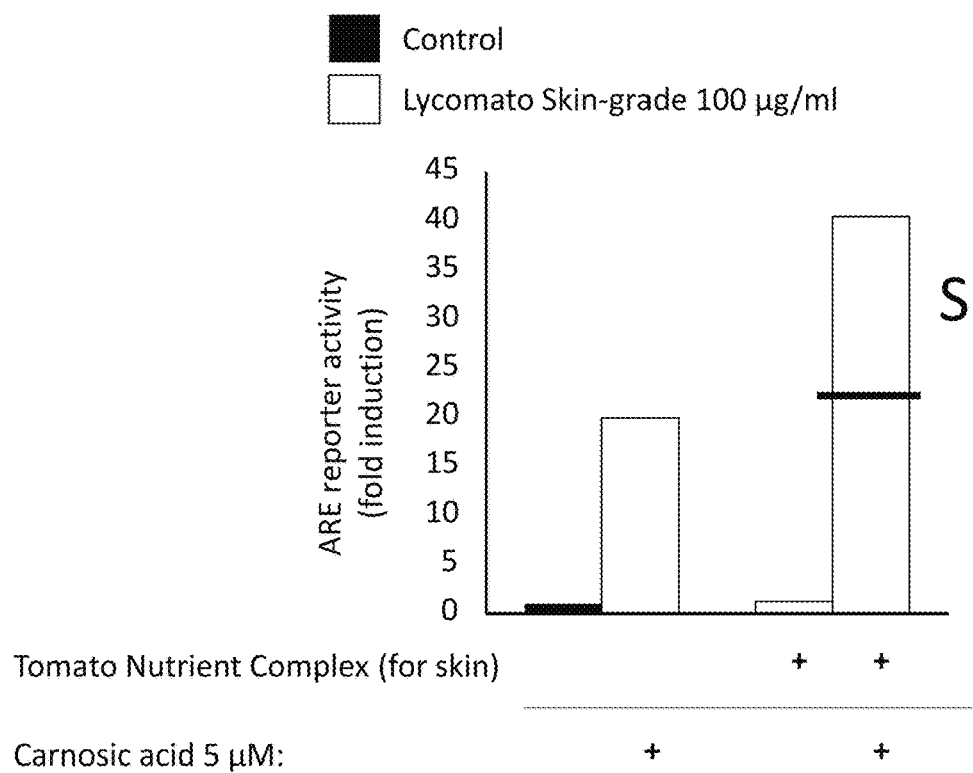

A similar synergistic activation of EpRE/ARE reporter activity by the Tomato Nutrient Complex and the Carnosic acid was evident in dermal fibroblasts (NHDF cells) (FIG. 7).

Example 6

Figure 8:
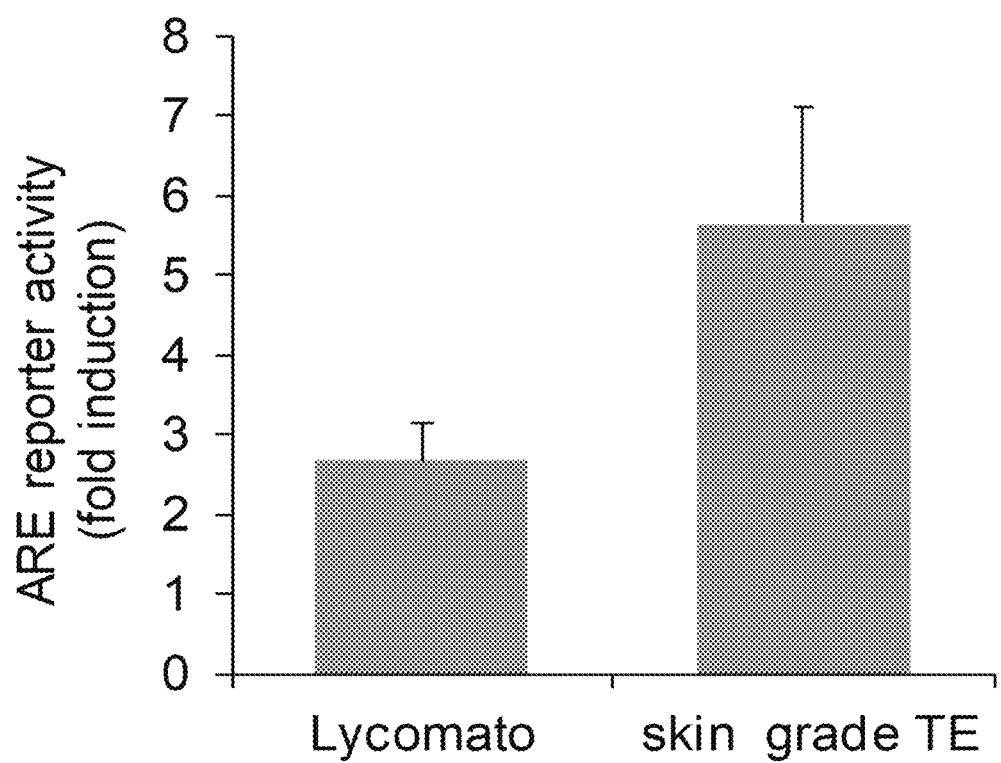
FIG. 8 is a bar graph showing the induction of EpRE/ARE reporter activity in human keratinocytes by two different preparations of Tomato Nutrient Complex.

Induction of EpRE/ARE Reporter Activity in Human Keratinocytes by Two Different Preparations of Tomato Nutrient Complex KERTr human keratinocytes were seeded in 24 well plates (60,000 cells/well) and EpRE/ARE reporter activity was measured by transfection with 0.2 µg 4×ARE reporter construct and 0.1 µg normalizing plasmid. ARE reporter activity was measured in cell extracts and normalized to renilla luciferase using the Dual Luciferase Reporter Assay System, (Promega, Madison, WI) according to the manufacturer's instructions. The tested compounds containing 10 µM lycopene were added 6 h after the transfection and incubated for additional 16-20 h. The results were normalized to cell number which was estimated by the crystal violet method. Results are the means±SEM of 3-4 experiments with 4 replicates in each experiment (FIG. 8).

ARE reporter activity of the $1^{st}$ generation (Lycomato) composition, which is described by U.S. Pat. No. 9,468,609B2 and is incorporated herein by reference, and the $2^{nd}$ generation, the herein disclosed composition which is part of the Lycoderm final composition (skin grade-tomato extract enriched with phytoene and phytofluene) was measured. The preparation skin grade tomato extract (skin grade TE), part of the Lycoderm product showed a higher ARE reporter activity. This preparation contains a higher proportion of phytoene and phytofluene compared to the $1^{st}$ generation (Lycomato).

Example 7

Improving Skin Lines/Wrinkles

A 16-week, double-blind, randomized, placebo-controlled clinical study to evaluate the efficacy of the oral product Lycoderm to improve skin parameters (e.g., condition and appearance). Data were analysed for changes in skin condition as evaluated via instrumentation, expert grading, image analysis and responses to subjective questionnaires. Additionally, laboratory evaluations included blood analysis. The test product was used by half of the panel, while the remainder of the panel used a placebo control. Subjects and study staff remained blinded to product identity for the duration of the study. A total of 60 subjects completed study participation. Study visits occurred up to approximately twenty-one days prior to baseline at screening/washout, at baseline and after four, eight, twelve and sixteen weeks (W4, W8, W12, W16).

Mean scores for a Lycoderm composition-treated cohort for the appearance of skin radiance/luminosity showed statistically significant improvement from baseline to weeks 4, 8, 12 and 16. Mean scores for the Lycoderm composition-treated cohort for the appearance of face skin lines/wrinkles (global) and lightening/brightening showed statistically significant improvement from baseline to weeks 4, 8 and 16.

Summarizing, the Lycoderm composition-treated cohort showed greater improvement in face lines/wrinkles (global) from week 16 (see table 1).

TABLE 1

Expert Clinical Grader Evaluation - Product Comparison

| Assessment | Time Point | n | Placebo (Product A) Mean Difference ± SD From BL Face | n | Lycoderm (Product B) Mean Difference ± SD From BL | $P_T$-Value A vs B |
|---|---|---|---|---|---|---|
| Lines/Wrinkles (Global) | Week 4 | 28 | −0.11 ± 0.66 | 31 | −0.39 ± 0.71 | 0.125 |
|  | Week 8 | 28 | −0.22 ± 0.71 | 31 | −0.46 ± 0.89 | 0.253 |
|  | Week 12 | 29 | −0.07 ± 0.57 | 31 | −0.24 ± 0.80 | 0.342 |
|  | Week 16 | 29 | 0.00 ± 0.61 | 31 | −0.39 ± 0.77 | $0.031^B$ |

[B]Product B outperformed Product A.

Example 8

Improving Carotenoid Level in the Palm Skin

The level of tissue carotenoid, e.g., lycopene, phytoene, and phytofluene, were quantified using a biophotonic scanner. The results revealed a statistically significant increase (improvement) from baseline of the mean tissue carotenoid level in the Lycoderm-composition treated cohort at every time interval examination, while no significant increase was detected for the placebo-treated cohort (see table 2). Comparison analysis of mean-difference-from-baseline scores for both cohorts revealed a statistically significant differences between results at all time interval examinations, where the Lycoderm-composition treated cohort's results were significantly more favourable than those from the placebo-treated cohort (see table 3).

TABLE 2

Instrumental Evaluation - Biophotonic Scanner, Comparison to Baseline

| | | Placebo (Product A) | | | | | Lycoderm (Product B) | | | |
| --- | --- | --- | --- | --- | --- | --- | --- | --- | --- | --- |
| Assessment | Time Point | n | Mean ± SD | Mean % Improvement From BL mean | % Subjects Showing Improvement From BL Palm | P-Value TX vs. BL | n | Mean ± SD | Mean % Improvement From BL mean | % of Subjects Showing Improvement From BL | P-Value TX vs. BL |
| Biophotonic Scanner | Baseline | 29 | 37344 ± 14223 | | | | 31 | 35290 ± 12879 | | | |
| | Week 4 | 28 | 37357 ± 11988 | 2.32% | 39.3% | 0.717 | 31 | 39935 ± 13107 | 15.14% | 67.7% | <0.001* |
| | Week 8 | 25^ | 34880 ± 10272 | 2.97% | 48.0% | 0.951 | 26 # | 42384 ± 16482 | 19.25% | 76.9% | 0.001* |
| | Week 12 | 25^ | 37800 ± 14916 | NI | 48.0% | 0.604 | 24 # | 46833 ± 16682 | 27.10% | 87.5% | <0.001* |
| | Week 16 | 29 | 38034.48 ± 13642.06 | 4.46% | 48.3% | 0.591 | 31 | 45774 ± 16016 | 31.19% | 80.6% | <0.001* |

NI = No Improvement
*Indicates a statistically significant improvement compared to baseline, $p \leq 0.05$
^Product A: Three subjects (#29, 30, and 36) did not have Week 8 data and four subjects (#36, 40, 46, and 47) did not have Week 12 data due to machine malfunction.
Product B: Six subjects (#32, 33, 34, 35, 36 and 63) did not have Week 8 data, and seven subjects (#33, 34, 35, 41, 42, 43 and 45) did not have Week 12 data.

TABLE 3

Instrumental Evaluation- Biophotonic Scanner, Product Comparison

| Assessment | Time Point | n | Placebo (Product A) Mean Difference ± SD From BL Palm | n | Lycoderm (Product B) Mean Difference ± SD From BL | $P_T$-Value A vs B |
| --- | --- | --- | --- | --- | --- | --- |
| Biophotonic Scanner | Week 4 | 28 | -464 ± 6697 | 31 | 4645 ± 5770 | 0.003$^B$ |
| | Week 8 | 25^ | -80 ± 6389 | 26# | 6538 ± 8372 | 0.003$^B$ |
| | Week 12 | 25^ | -2750 ± 14958 | 24# | 9583 ± 7988 | <0.001$^B$ |
| | Week 16 | 29 | 689 ± 6830 | 31 | 10483 ± 9131 | <0.001$^B$ |

^Product A: Three subjects (#29, 30, and 36) did not have Week 8 data and four subjects (#36, 40, 46, and 47) did not have Week 12 data due to machine malfunction.
Product B: Six subjects (#32, 33, 34, 35, 36 and 63) did not have Week 8 data, and seven subjects (#33, 34, 35, 41, 42, 43 and 45) did not have Week 12 data.
$^B$Product B outperformed Product A.

What is claimed is:

1. A method for improving one or more skin parameters in a subject in need thereof, comprising the step of administering to said subject a therapeutically effective amount of a composition comprising (a) lycopene; (b) phytoene and phytofluene; and (c) carnosic acid, wherein the weight ratio of (a) to (b) is from 1:0.3 to 1:0.6 and the weight ratio of (a) to (c) is from 1:0.1 to 1:0.4, and wherein said composition synergistically inhibits ultraviolet B (UVB)-induced interleukin 6 (IL-6) release, thereby improving one or more skin parameters in the subject.

2. The method of claim 1, further comprising a step of determining the level of a carotenoid in the skin of a subject, wherein a reduced level of said carotenoid in the skin of said subject compared to a control baseline is indicative of said subject being suitable for administering with said composition.

3. The method of claim 1, wherein said subject is afflicted with a reduced level of a carotenoid.

4. The method of claim 1, wherein said one or more skin parameters are selected from the group consisting of: face lines/wrinkles, mean skin carotenoid level, skin luminosity, skin radiance, and ultra-violet (UV)-induced damage.

5. The method of claim 1, wherein said skin is the palm skin.

6. The method of claim 4, wherein said improving UV-induced damage in a subject comprises preventing or treating a skin-related condition caused by UV radiation in said subject.

7. The method of claim 6, wherein said treating comprises inhibiting the production of tumor necrosis factor alpha (TNF-α), interleukin 6 (IL-6), erythema reduction, or any combination thereof, in said subject.

8. The method of claim 1, wherein the weight ratio of (a) and (c) is from 1:0.2 to 1:0.4.

9. The method of claim 1, wherein said composition further comprises tocopherol, and wherein the weight ratio of lycopene and tocopherol is from 1:0.3 to 1:0.5.

10. The method of claim 1, wherein said composition further comprises beta-carotene, and wherein the weight ratio of lycopene and beta-carotene is from, 1:0.03 to 1:0.06.

11. The method of claim 1, wherein said composition is an oral composition.

12. The method of claim 1, wherein said composition further comprises a nutraceutical, a cosmeceutical, or a pharmaceutical acceptable excipient.

13. The method of claim 1, wherein said composition is a cosmeceutical composition.

14. The method of claim 1, wherein said composition is an anti-wrinkles composition.

15. A method for synergistically inhibiting UVB-induced IL-6 release in a subject in need thereof, comprising the step of administering to said subject an effective amount of a composition comprising (a) lycopene; (b) phytoene and phytofluene; and (c) carnosic acid, wherein the weight ratio of (a) to (b) is from 1:0.3 to 1:0.6 and the weight ratio of (a) to (c) is from 1:0.1 to 1:0.4, thereby synergistically inhibiting UVB-induced IL-6 release in the subject.

\* \* \* \* \*